US009333307B2

(12) United States Patent
Schwaiger et al.

(10) Patent No.: US 9,333,307 B2
(45) Date of Patent: May 10, 2016

(54) INJECTION DEVICE FOR INJECTION INTO BIOLOGICAL TISSUE AND INJECTION DEPOT

(75) Inventors: Wolfgang Schwaiger, Innsbruck (AT); Rainer Marksteiner, Schwaz (AT)

(73) Assignee: INNOVACELL BIOTECHNOLOGIE AG, Innsbruck (AT)

( * ) Notice: Subject to any disclaimer, the term of this patent is extended or adjusted under 35 U.S.C. 154(b) by 1008 days.

(21) Appl. No.: 12/670,283

(22) PCT Filed: Jul. 25, 2008

(86) PCT No.: PCT/EP2008/006143
§ 371 (c)(1),
(2), (4) Date: Jun. 17, 2010

(87) PCT Pub. No.: WO2009/013011
PCT Pub. Date: Jan. 29, 2009

(65) Prior Publication Data
US 2010/0278785 A1    Nov. 4, 2010

(30) Foreign Application Priority Data

Jul. 25, 2007    (DE) .......................... 10 2007 034 682

(51) Int. Cl.
*A61M 5/32*    (2006.01)
*A61M 5/42*    (2006.01)
*A61K 9/00*    (2006.01)

(52) U.S. Cl.
CPC ............ *A61M 5/3287* (2013.01); *A61K 9/0019* (2013.01); *A61M 5/427* (2013.01)

(58) Field of Classification Search
CPC .... A61B 8/12; A61M 5/46; A61M 2005/206; A61M 2005/341; A61M 5/16831; A61M 5/32; A61M 5/3287; A61M 5/427; A61K 9/0019

USPC ................. 604/181, 522, 117, 116, 223, 131, 604/207–211
See application file for complete search history.

(56) References Cited

U.S. PATENT DOCUMENTS

| 4,613,328 A | 9/1986 | Boyd |
| 5,336,201 A * | 8/1994 | von der Decken .. A61M 5/1424 128/DIG. 12 |

(Continued)

FOREIGN PATENT DOCUMENTS

| CA | 1228519 A1 | 10/1987 |
| CA | 2391685 A1 | 12/2002 |

(Continued)

OTHER PUBLICATIONS

Corresponding Russian application 2010106640/14(009347) Decision to Grant Mar. 12, 2013 with German translation.

*Primary Examiner* — Emily Schmidt
*Assistant Examiner* — Lauren M Peng
(74) *Attorney, Agent, or Firm* — Duane Morris LLP (57) ABSTRACT

An injection device (100), provided for injection with an injection syringe (50) into an organism (1), comprises a guide device (10) designed to receive the injection syringe (50), wherein an injection needle (51) and a syringe body (52) of the injection syringe (50) can be moved relative to the guide device (10), in an advance movement towards or in a withdrawal movement away from the organism (1), and an actuating device (20) to which the injection syringe (50) can be coupled and which is used to actuate the injection syringe (50) for injection of an injectable substance into the organism (1), wherein the actuating device (20) has an actuating element (21) which forms an abutment for a piston device (53) of the injection syringe (50) on the guide device (10), in such a way that, during the withdrawal movement, the piston device (53) executes a relative movement counter to the injection needle (51) and the syringe body (52).

21 Claims, 5 Drawing Sheets

(56) References Cited

U.S. PATENT DOCUMENTS

| | | |
|---|---|---|
| 6,309,374 B1 | 10/2001 | Hecker et al. |
| 6,575,936 B1 * | 6/2003 | Kojima et al. ............... 604/155 |
| 2004/0092821 A1 | 5/2004 | Hering et al. |
| 2005/0085790 A1 * | 4/2005 | Guest et al. .................. 604/506 |
| 2005/0124940 A1 | 6/2005 | Martin et al. |
| 2009/0234319 A1 | 9/2009 | Marksteiner |

FOREIGN PATENT DOCUMENTS

| | | |
|---|---|---|
| EA | 6960 B1 | 6/2006 |
| FR | 2895631 A1 | 7/2007 |
| FR | 2895681 A1 * | 7/2007 |
| JP | 2007143635 A | 6/2007 |
| RU | 2006106269 A1 | 6/2006 |
| WO | 0245588 A1 | 6/2002 |
| WO | 2006128718 A1 | 12/2006 |

* cited by examiner

INJECTION DEVICE FOR INJECTION INTO BIOLOGICAL TISSUE AND INJECTION DEPOT

The invention relates to an injection device, which is adapted for the positioning and actuation of an injection syringe, medical equipment that is provided with said injection device, methods for injecting an injectable substance into biological tissue, in particular into muscle tissue of a human being, and an injection depot in biological tissue.

Injecting a biologically active injectable substance into biological tissue is known, for example in order to achieve a pharmacological action or to influence cell growth or differentiation in the tissue. The injection is carried out with an injection needle with simultaneous observation of the tissue, for example with an ultrasonic probe. For practical medical applications, a precise positioning of the injection needle is of considerable importance, in order to deposit the injectable substance exactly at a desired injection site and to minimize the risk of damage to the surrounding tissue.

For positioning the injection needle, an injection device with a needle guide is used, which has a predetermined position and orientation relative to the ultrasonic probe. WO 02/45588 A1 and DE 10 2005 025 539 A1 describe injection systems that have an ultrasonic probe and an injection device with a needle guide. Conventional injection systems are intended for injection through the inner wall of body cavities or tubes, e.g. into the urethra. For this purpose, the needle guide has curvature that is directed radially outwards relative to the axial orientation of the ultrasonic probe. The injection site in the tissue is determined by the curvature of the needle guide and the length of protrusion of an injection needle that is pushed through the needle guide and into the tissue.

Injection with conventional injection systems is carried out by introducing the injection device together with the ultrasonic probe through a body opening and positioning it in the body. The injection needle is advanced up to a predetermined injection site. In this state, injection of the injectable substance takes place at the injection site, with formation of a spherical depot in the tissue. Then the needle is withdrawn and the injection device is arranged again for another injection at a different injection site. Injection at a plurality of injection sites, in particular along a tissue extending longitudinally along a tubular hollow organ therefore requires a plurality of injection steps, in which a new injection site is alternately set and the injectable substance is deposited at the set injection site. The formation of a plurality of punctures can be unfavourable owing to scarring and hence destabilization of the hollow organ being treated.

The conventional injection systems did indeed represent an advance for the exact deposition of biologically active substances in a tissue. There is the disadvantage, however, that application of the conventional injection systems is restricted to injection through the inner wall of body cavities or tubes. In medical practice, the conventional injection systems are not suitable for injection through the outer surface of the body. Injection through the inner wall may, however, be undesirable, for example on medical reasons. For example, for injection in the sphincter muscle of the rectum, the conventional injection systems would have the disadvantage that piercing of the mucous membrane (mucosa) would present a high risk of infection. This disadvantage is further intensified by the restriction to spherical depots, as injection at a plurality of injection sites would require many punctures through the inner wall in the body.

Because of these disadvantages, the conventional injection systems are in particular unsuitable for injection in the sphincter muscle of the rectum. The sphincter muscle of the rectum essentially comprises the parts mucosa, internal sphincter, external sphincter and puborectal muscle (musculus puborectalis). The external sphincter merges into the puborectal muscle, which in its turn, with the pubococcygeus muscle and the iliococcygeus muscle, forms the levator ani muscle (part of the pelvic diaphragm). The mucosa is a mucous membrane layer with a very good blood supply and several types of tissue, which lines the inner wall of the intestine and serves as a "seal" of the rectum. Damage to this coating layer may lead to faecal incontinence (e.g. haemorrhoidectomy). The internal sphincter muscle (internal sphincter) is a muscle consisting of smooth muscle cells, which is arranged around the rectum. The external sphincter muscle (external sphincter) is a muscle consisting of skeletal muscle cells, positioned externally around the internal sphincter. Both sphincter muscles are important for faecal continence, with the pelvic diaphragm and the anorectal angle (angle between rectum/colon) also fulfilling an additional function for the closure mechanism.

As a result of overstraining or surgical procedures, the aforementioned tracts of muscles may sustain injuries, possibly leading to faecal incontinence. For example, the external sphincter muscle has an area of reduced thickness, where damage can occur, especially in women as a result of parturition. This leads to scarring of the muscle, which is no longer able to perform its function, so that faecal incontinence develops.

Conventional methods for treating faecal incontinence are based on pelvic floor exercises (conservative) or on an overlapping operation, in which breaks in the sphincter are overlapped and sutured or an artificial sphincter is implanted. Often, however, the conservative treatment is no longer adequate, whereas the surgical procedures are risky and unreliable.

Treatments with filler materials, in which fillers are injected in muscles (so-called "bulk injection"), are known from medical practice. However, these treatments with fillers have the disadvantage that the muscle tissue is stretched by internal pressure of the filler material and can be damaged as a result.

The objective of the invention is to provide an improved injection device for an injection syringe, with which the disadvantages and limitations of the conventional techniques are overcome and which is, in particular, suitable for injection in a sphincter muscle of the rectum. Another objective of the invention is to provide improved medical equipment, which has said injection device, and an improved method of injection, with which the disadvantages of the conventional methods of injection are overcome.

These objectives are solved by an injection device, medical equipment, a method of injection and/or an injection depot with the features of the independent claims. Advantageous embodiments and uses of the invention can be seen from the dependent claims.

With respect to the device, the objective is solved, according to a first aspect of the invention, by the general technical teaching of providing an injection device with a guide device, into which an injection syringe can be inserted, and an actuating device, which acts together with an injection syringe inserted in the guide device, so that with a withdrawal movement of the injection syringe an expulsion of an injection fluid occurs. The actuating device has an actuating element, which forms a limit stop for a piston device of the injection syringe. The actuating element is arranged, relative to the guide device, stationary or displaceable at a speed that differs from the speed of the withdrawal movement. Advantageously, the injection device according to the invention makes it possible for the withdrawal movement of the injection syringe, in particular an injection needle and a syringe body, to cause injection of an injectable substance contained in the syringe body. The piston device performs, during the withdrawal movement, a relative movement opposite to the injection needle and the syringe body. Advantageously, the invention offers the possibility of gentle injection into the space created in the tissue by the injection needle during withdrawal. The cells deposited along an injection path remain viable, making possible effective growth in the tissue.

According to a second aspect, the aforementioned objective is solved by the general technical teaching of providing a medical equipment that comprises the injection device according to the invention and an injection syringe inserted therein. Advantageously, the medical equipment according to the invention has, in comparison with the conventional injection systems, a novel functionality, because with the injection syringe, simultaneously with the withdrawal movement, linear injection depots can be formed reliably.

Here, the term "injection syringe" means generally any fluid delivery device with a fluid reservoir (syringe body with at least one chamber), an injection cannula (hollow syringe needle) and a piston device with at least one syringe piston and at least one piston stem. The syringe needle can be straight or curved. The syringe body can comprise one or more chambers, which are preferably cylindrical. Each of the chambers is adapted to receive a syringe piston. By displacement of the at least one syringe piston in the syringe body, fluid can be expelled from the syringe body through the syringe needle. The injection syringe can for example comprise a syringe body with a single chamber, to which the syringe needle is connected and in which a syringe piston is arranged, or two or more chambers, to which the syringe needle is connected and in which in each case a syringe piston is arranged. According to the invention, the syringe needle can additionally be used as an electromyography probe (EMG probe), to conduct electrical signals from the tissue in which the injection takes place.

Here, the term "injectable substance" denotes generally any fluid that contains at least one pharmacologically or biologically active substance in dissolved or suspended form. According to a preferred application of the invention, the injectable substance comprises a cellular suspension, in particular a myoblast suspension.

According to a third aspect, the objective of the invention is solved, with respect to the method, by the general technical teaching of depositing an injectable substance in an organism using the injection device according to the invention and an injection syringe, in which injection of the injectable substance takes place during a withdrawal movement of the injection syringe from the organism. For this, preferably the guide device is first aligned relative to the organism, then the injection syringe is inserted in the guide device and is advanced into the organism and finally the syringe body and the injection needle of the injection syringe are withdrawn together, and during withdrawal, the syringe piston of the injection syringe is actuated with the actuating element of the injection device according to the invention.

Advantageously, according to the invention a new deposition principle is realized, in which the injectable substance is deposited in an injection channel formed in the organism by the syringe needle. The actuating device, with the actuating element that is operative exclusively during the withdrawal movement, makes it possible, in contrast to the conventional production of spherical depots, to form linear injections. Larger amounts of the injectable substance can be deposited in the tissue very efficiently after a single positioning of the injection needle in the tissue and a single puncture.

Therefore the objective of the invention is solved, according to further aspects, by a linearly formed injection depot (cellular implant), in particular of autologous myoblasts, e.g. with autologous serum, in a biological tissue; the use of autologous myoblasts, e.g. with autologous serum, in the form of a linear injection volume, which is arranged in a sphincter muscle of the rectum, for the treatment of faecal incontinence; the use of autologous myoblasts, e.g. with autologous serum, for the production of a linear injection volume, which is arranged in a sphincter muscle of the rectum, for the treatment of faecal incontinence; and a method of production of a medicinal product for the treatment of faecal incontinence, using, as a constituent of the medicinal product, autologous myoblasts, e.g. with autologous serum. The terms "linear injection volume" or "linear injection depot" generally denote a track-shaped, strip-shaped or thread-shaped arrangement of a substance (cellular implant) with a longitudinal dimension that is larger than the transverse dimension of the arrangement of the substance.

The formation, according to the invention, of a linear cellular implant with living cells has the particular advantage of a uniform distribution of the cells in the tissue, which leads to particularly good growth of the cells.

According to a preferred embodiment of the injection device according to the invention, the actuating element is arranged so that, during the advance movement of the injection needle and of the syringe body, the syringe piston can move freely. Advantageously, this can facilitate the insertion of the injection syringe into the injection device. Preferably, the actuating device is provided with a positioning device, via which the actuating element is connected to the guide device.

The positioning device can advantageously fulfil several functions. For example, for movement of the actuating element, the positioning device can be moved between a release position, in which the syringe piston can move freely during the advance movement of the injection syringe, and a stop position, in which the syringe piston is actuated during the withdrawal movement. For this purpose, the positioning device has for example a swivelling lever, with which the actuating element can be swivelled relative to the guide device. By means of the swivelling lever, the actuating element can be moved between the aforementioned release and stop positions.

In addition, the positioning device can contain a translation element, with which the actuating element in the stop position can be displaced relative to the guide device. By means of the translation element, the position of the actuating element can be adjusted to the size and design of the injection syringe actually used. Moreover, the actuating element can be displaced with the translation element during the withdrawal movement of the injection syringe. In particular it is possible to set a speed of the translation element that is less than the speed of the withdrawal movement or is opposite to the latter. For this, the translation element is preferably provided with a transmission mechanism, with which the speed of the actuating element can be adjusted relative to the speed of the injection needle and of the syringe body. Alternatively or additionally, the translation element can be provided for displacement of the actuating element between the release and stop positions.

According to another advantageous embodiment of the invention, the translation element can be provided with a motorized drive, with which the actuating element can be displaced relative to the guide device. In this case, advantageously, the actuation of the syringe piston can be set independently of the speed of the withdrawal movement of the injection needle and of the syringe body.

According to an especially preferred embodiment of the invention, the guide device is adapted for setting an injection angle of the injection syringe. The injection angle (puncture angle, angle of inclination) is the angle between the longitudinal direction of a hollow organ, e.g. of the rectum, in whose wall an injectable substance is to be introduced, and the injection needle, in particular the angle between the longitudinal direction of an imaging probe, which is introduced into the hollow organ, and the injection needle. According to the invention, the injection angle is preferably selected such that the injection needle is directed parallel to the longitudinal direction or radially inwards, i.e. towards the centre of the hollow organ, in particular of the imaging probe. This permits reliable injection from outside the organism into the wall of the hollow organ.

Preferably the guide device of the injection device comprises a carrier part, which is provided with a swivelling guide tube for receiving the injection needle. The guide tube can allow adjustment of the injection angle of the injection syringe.

Advantageously, the guide tube is sufficient for stable retention of the injection syringe on the guide device. By swivelling the guide tube, it is possible to select the injection angle of the injection needle in an organism, on which the injection device with the guide device is placed. Advantageously, the injection angle also allows variable setting of the puncture depth in the tissue.

Preferably the guide tube is positioned in the guide device with a pivot bearing and a translational bearing, the injection angle of the injection needle being adjustable by displacing the translational bearing relative to the pivot bearing which turns freely with it.

The stability of retention of the injection syringe on the guide device can, according to a variant of the invention, advantageously be improved if a swivelling lever of the actuating device forms a carrier for the injection syringe. The swivelling lever and the guide tube are, in this embodiment of the invention, arranged so that when the syringe needle is arranged in the guide tube, the syringe body lies on the swivelling lever. By turning the swivelling lever, it is possible to adjust the injection angle of the syringe needle.

Further advantages can be obtained when the guide device is connected to a holding plate. A front side of the holding plate can be placed on the organism, while the guide device is secured on a rear side of the holding plate. The holding plate contains at least one through-hole, through which the injection needle can protrude from the guide device to the organism. Advantageously, the holding plate facilitates orientation of the guide device relative to the organism. With a plane direction of extension of the holding plate, a predetermined radial reference plane is defined. The injection syringe, inserted in the guide device, is displaceable in an axial reference direction (perpendicular to the radial reference plane) or with the predetermined injection angle relative to the axial reference direction.

For setting various injection sites it may be advantageous if the holding plate is a movable, in particular rotatable part of a stationary holding device.

Alternatively or additionally, a plurality of through-holes can be formed in the holding plate, each of which is provided for orientation of the injection needle relative to a particular injection site.

According to another advantageous embodiment of the invention, the injection device can be provided with an imaging probe, in particular an ultrasonic probe. The guide device can be arranged displaceably on the imaging probe. Especially preferably, the imaging probe is arranged displaceably on the holding plate. For this purpose, the holding plate has in particular a probe holder, in which the imaging probe can be inserted.

Further details and advantages of the invention can be seen from the following description of preferred embodiments of the invention and the appended drawings, showing.

Embodiments of the invention are explained in the following, referring for example to injection with an injection syringe that has a syringe body with one chamber and a piston device with one syringe piston. The practical implementation of the invention is not restricted to this application, but is correspondingly also possible with an injection syringe that comprises two or more syringe pistons in two or more chambers, whose contents are mixed during injection.

Figure 1:
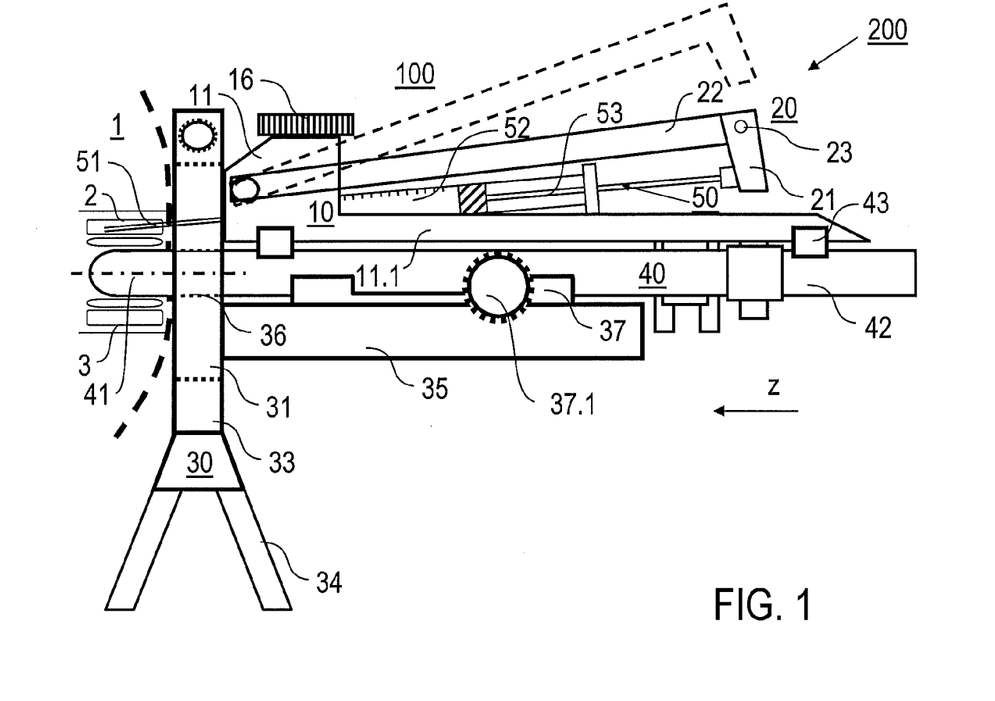
FIG. 1: a schematic side view of a first embodiment of the injection device according to the invention with an injection syringe.

The first embodiment of the injection device 100 according to the invention shown in FIG. 1 comprises the guide device 10 with a carrier part 11 and a carrier arm 11.1, the actuating device 20 with the actuating element 21 and the swivelling lever 22, the holding device 30 with the holding plate 31, a plate frame 33, a stand 34 and a holding arm 35, and the ultrasonic probe 40 with an ultrasonic head 41 and a shaft 42. The medical equipment 200 according to the invention is formed by the combination of the injection device 100 with the injection syringe 50, comprising the injection needle 51, the syringe body 52 and the piston device 53 (syringe piston 53), inserted in the guide device 10. The injection syringe 50 has an injection volume of e.g. 1 ml. In the example shown, the radial reference plane of the holding plate 31 is designated as the x-y plane. The axial reference direction of the injection device 100 and in particular of the ultrasonic probe 40 runs in the z-direction. The ultrasonic probe 40 is connected in a manner known per se to an ultrasound unit (not shown), with which images of the tissue can be acquired and displayed.

FIG. 1 also shows the orientation of the injection device 100 relative to an organism 1, in particular the external sphincter muscle 2 of the rectum 3 (drawn schematically, not to scale). The axial length of the sphincter muscles is e.g. approx. 2.5 cm. The radial thicknesses of the internal and external sphincter muscle are e.g. approx. 2 mm or approx. 5 mm.

The carrier part 11 of the guide device 10 forms a holder for the injection syringe 50, in particular the injection needle 51. Further details of the carrier part 11 are shown schematically in FIG. 2. The carrier part 11 is a component in which a guide tube 12 is arranged. The carrier part 11 is for example made of plastic. The guide tube 12 is a metal tube, e.g. made of stainless steel or brass, with an inside diameter that is selected for positively receiving the injection needle 51. The guide tube 12 fulfils a dual function, in that it establishes the injection angle α (angle of inclination of the injection needle 51 relative to the axial reference direction) and forms a guide for the displacement of the injection syringe. The injection angle α forms, reckoned from the axial reference direction, an acute angle, preferably in the range from 0° to 45°. For reliable guidance of the injection syringe, the guide tube 12 preferably has a length in the range from 5 mm to 8 cm. The length of the guide tube 12 is moreover selected to ensure a defined maximum insertion depth of the injection needle 51.

The insertion depth of the injection needle 51 is selected according to the desired use of the injection device according to the invention. Advantageously, large insertion depths are possible, permitting injection into the puborectal muscle.

Figure 2:
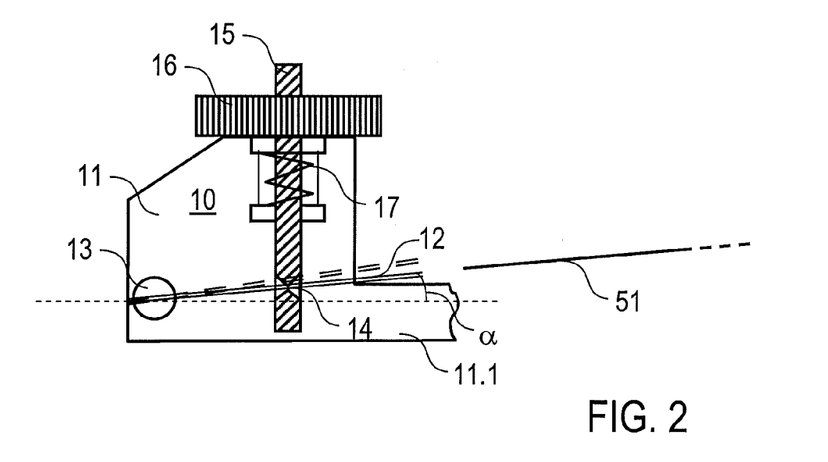
FIG. 2: an enlarged view of the guide device shown in FIG. 1.

The injection angle α also sets the puncture depth in the tissue. The structure according to FIG. 2 is for example adapted so that, by displacement of the translational bearing, the radial puncture depth in the tissue can be varied over a range of 6 mm.

The guide tube 12 can be swivelled relative to the axial reference direction (z-direction). For this, the guide tube 12 is mounted in a pivot bearing 13 (ball joint) and a translational bearing 14. The pivot bearing 13 is arranged on a front side of the carrier part 11, directed towards the holding plate 31 in the direction of injection, and is adapted for rotation about an axis perpendicular to the axial reference direction. The translational bearing 14 is formed in a threaded bar 15 at a distance from the pivot bearing 13. The threaded bar 15 can be displaced radially by turning an adjusting screw 16 on an upper side of the carrier part 11, to set the angle of inclination of the guide tube 12. For a movement radially outwards, the threaded bar 15 is pushed out of the carrier part 11. The opposite movement radially inwards is supported by a return spring 17 in the carrier part 11. Departing from the illustration in FIG. 2, the adjusting screw 16 can be provided in the middle or on an underside of the carrier part 11.

The actuating element 21 of the actuating device 20 is arranged via the swivelling lever 22 swivelling on the carrier part 11 (FIG. 1). The actuating element 21 and the swivelling lever 22 are for example made of plastic. The actuating device 20 can be swivelled radially between a release position (drawn with dashed lines) and a stop position (drawn with solid lines). In the release position, the injection syringe 50, charged with an injectable substance, and therefore with the injection piston 53 retracted in the syringe body, can be inserted in the guide device 10. Then the actuating device 20 can be swivelled to the stop position. In this position, the actuating element 21 is at the free end of the injection piston 53.

The actuating element 21 forms an abutment for the injection piston 53. Alternatively or additionally to the ability of the swivelling lever 22 to swivel on the carrier part 11, the actuating element 21 can swivel on the swivelling lever 22, to simplify orientation of the actuating element 21 relative to the inserted injection syringe 50 (see FIG. 4). The actuating element 21 can in this case be fixed relative to the swivelling lever 22 with a fixing screw 23.

The ultrasonic probe 40 is arranged on the holding arm 35 of the holding device 30 in such a way that the ultrasonic head 41 and the shaft 42 extend in the axial reference direction. The ultrasonic probe 40 is a transrectal probe, in particular with a shaft diameter in the range from 1 to 2 cm, e.g. of type 8818 from B-K Medical. The ultrasonic head 41 is preferably set up for imaging along a transverse acoustic plane (parallel to the x-y plane) and along a longitudinal acoustic plane (radially).

The ultrasonic probe 40 is arranged on the holding arm 35 displaceably in the axial direction. For this, for example a slide 37 is provided, to which the ultrasonic probe 40 is connected firmly, and which can be displaced on a rail (not shown) in holding arm 35. By actuating a slide screw 37.1, the ultrasonic probe 40 can be displaced in the axial direction and/or can be fixed.

Figure 3:
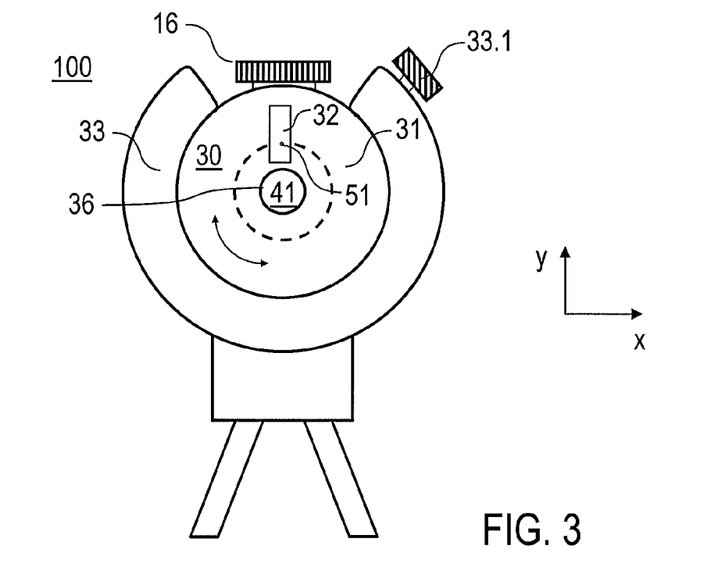
FIG. 3: a schematic front view of the embodiment of the injection device according to the invention shown in FIG. 1.

FIG. 3 shows the front view of the injection device 100, in particular of the holding device 30. The holding plate 31 has a front, which is placed on the organism 1, and a back, on which the guide device 10 is secured. A through-hole 32, through which the injection needle 51 passes, and a probe holder 36, are provided in the holding plate 31. The holding plate 31 is arranged rotatably in the plate frame 33. With the holding plate 31, the guide device 10 can be rotated about the longitudinal axis of the ultrasonic probe 40. The azimuthal position of the injection needle 51 relative to the organism can be set by rotating the holding plate 31 and can be fixed with a frame screw 33.1.

The guide device 10 can be joined firmly to the back of the holding plate 31. In this case the carrier arm 12 is not joined firmly to the ultrasonic probe 40, instead only a shiftable support 43 is provided. Alternatively the guide device 10 can be connected exclusively via the ultrasonic probe 40 and the holding arm 35 to the holding plate 31. In this case a displacing device (not shown) is provided on the ultrasonic probe 40 for displacing and fixing the guide device 10 on the ultrasonic probe 40. The displacing device can for example comprise a combination of a slide and guide rails.

The injection, according to the invention, of an injectable substance into the organism 1, in particular the external sphincter muscle 2 of the rectum 3 (schematic, not drawn to scale) comprises the following steps. First, in an examination step, the holding plate 31 is placed on the organism 1. The ultrasonic probe 40 is introduced into the anus through the holding plate 30 and is fixed relative to the holding plate 31. The sphincter muscle tissue is examined with the ultrasonic probe 40, in order to establish the position and orientation of the defect to be treated and hence the desired injection site in the sphincter muscle.

This is followed by a calibration step with adjustment of the guide device 10. The guide device 10 is aligned relative to the holding plate 31 so that the injection needle of an injection syringe inserted in the guide device 10 would have its opening at the injection site. For calibration, the injection device 100 with the inserted injection syringe and the ultrasonic probe 40 is immersed in a water bath.

For the subsequent injection, first the holding device 30 (without the injection syringe) and the organism 1 are positioned relative to one another. The ultrasonic probe 40 is introduced into the anus. The holding plate 31 is rotated so that the guide device 10, in particular the guide tube 12, is directed on the desired injection site. Then the injection syringe 50 is inserted in the guide device 10 and is advanced until the injection needle 51 reaches the injection site in the tissue. By inserting the injection needle 51 into the tissue, an injection channel (puncture channel) is opened up, and will be filled with the injectable substance during subsequent injection. The injection needle 51 is advanced, with ultrasonic monitoring, up to the injection site, where the supply of the injectable substance is to begin. In the ultrasound unit, during introduction of the injection needle 51, images of the tissue are acquired and displayed, and optionally, supplementary puncture lines during display of the images can facilitate positioning.

In the next step, the actuating element 21 is aligned relative to the syringe piston 53. The swivelling lever 22 is applied to the injection syringe 50 and the actuating element 21 is fixed as abutment for the syringe piston 53. Then injection according to the invention takes place, by withdrawing the injection syringe 50, in particular the injection needle 51 and the syringe body 52, while keeping the injection piston 53 stationary. As a result, the injection piston 53 moves in the opposite direction relative to the injection needle 51 and the syringe body 52, so that withdrawal of the injection syringe 50 brings about injection into the tissue. Simultaneously with the withdrawal movement, the injection channel is filled. A linear injection volume is formed in the tissue. The injection takes place in tracks—i.e. the injection needle 51 is inserted to the deepest point in the tissue and is then withdrawn. During this withdrawal, a cell track is applied. The withdrawal movement of the syringe body 52 with the injection needle 51 can be effected manually in particular by pulling on the syringe body, with a positioning wheel (not shown) or with a motorized drive arranged on the guide device 10 (see also FIG. 6). After injection, the injection device is aligned again, in order to fill at least one further injection channel with injectable substance, especially cells.

Figure 4:
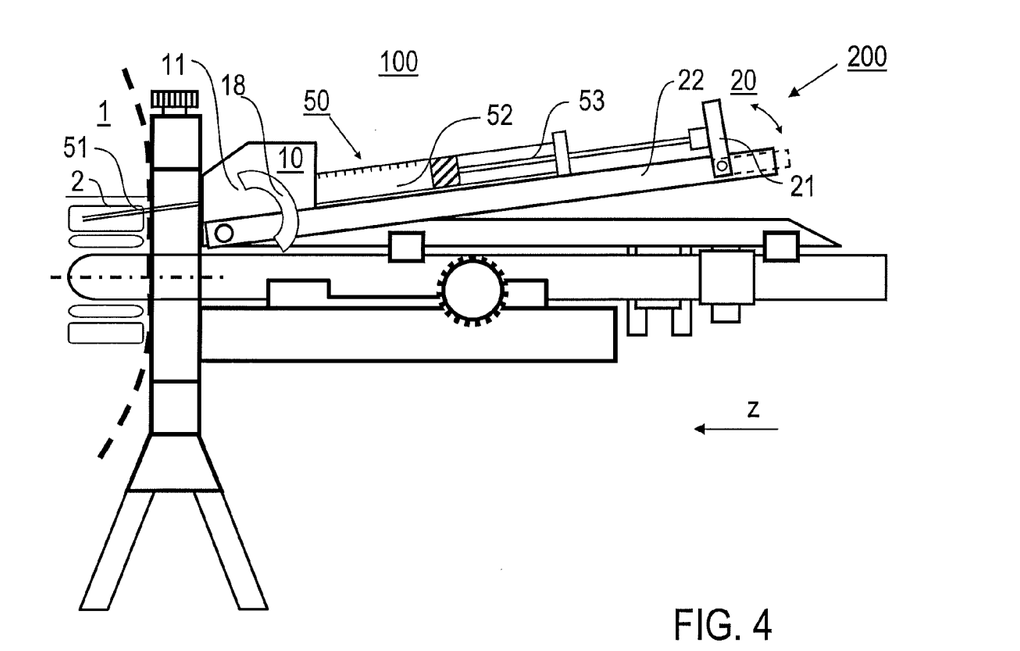
FIG. 4: a schematic side view of another embodiment of the injection device according to the invention.

FIG. 4 shows another embodiment of the injection device 100 according to the invention, which differs from the variant according to FIG. 1 in particular by the setting of the injection angle. According to FIG. 4, the swivelling lever 22 of the actuating device 20 forms a carrier arm for supporting the injection syringe 50. The injection syringe 50 is arranged displaceably on the swivelling lever 22 (see double-headed arrow A in FIGS. 5 and 6). The swivelling lever 22 has a swivel joint on the carrier part 11 of the guide device 10. The injection angle of the injection syringe can be set by swivelling the swivelling lever 22 relative to the carrier arm 11.1 (see double-headed arrow B in FIGS. 5 and 6). For this purpose, a clamping element 18, with which the swivelling lever 22 can be fixed, is provided on the carrier part 11. This embodiment of the injection device 100 has the advantage of simplified and particularly reliable setting or adjustment of the injection angle.

With the embodiment shown in FIG. 4, the injection angle is set during the aforementioned calibration step with the swivelling lever 22, with the actuating element 21 in a folded-back release position (drawn with dashed lines). For injection, after inserting the injection syringe 50 into the guide device 10 and on the swivelling lever 22 and insertion of the injection needle into the tissue, the actuating element 21 is swivelled forward, to form the limit stop for the injection piston 53. The withdrawal of the injection needle 51 and of the syringe body 52 (manually or with a motorized drive) results in formation of the linear injection volume in the tissue.

The syringe needle 51 can be guided in the carrier part 11 with a guide tube 12 or a stop ring 12.1. These variants are shown schematically in FIGS. 5 and 6. The guide tube 12 or the stop ring 12.1 performs a dual function, i.e. firstly guiding the syringe needle 51 and secondly formation of a front stop for the syringe body 52 of the injection syringe. On inserting the injection syringe in the guide device it is advanced, until the syringe body 52 is up against the guide tube 12 or the stop ring 12.1.

Figure 5:
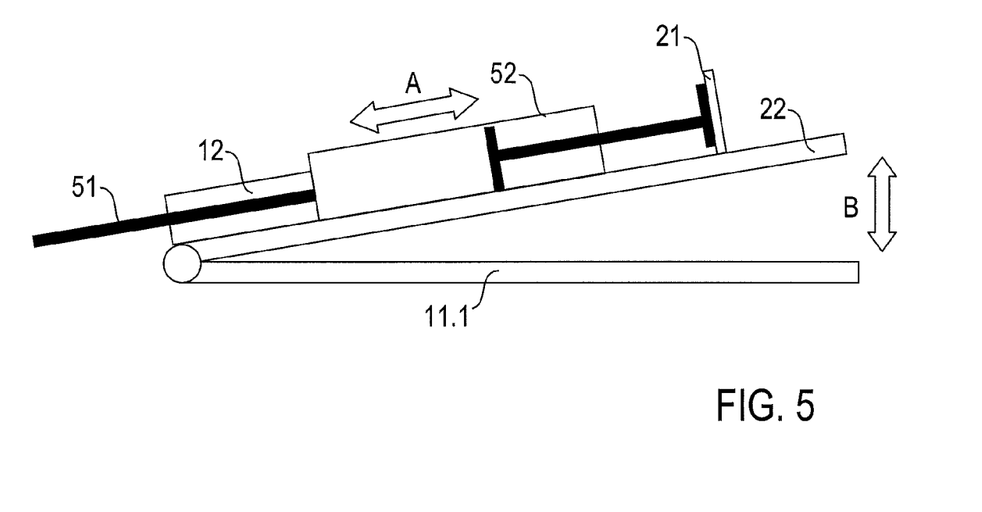
FIGS. 5 and 6: schematic side views of variants of the injection device shown in FIG. 4.
Figure 6:
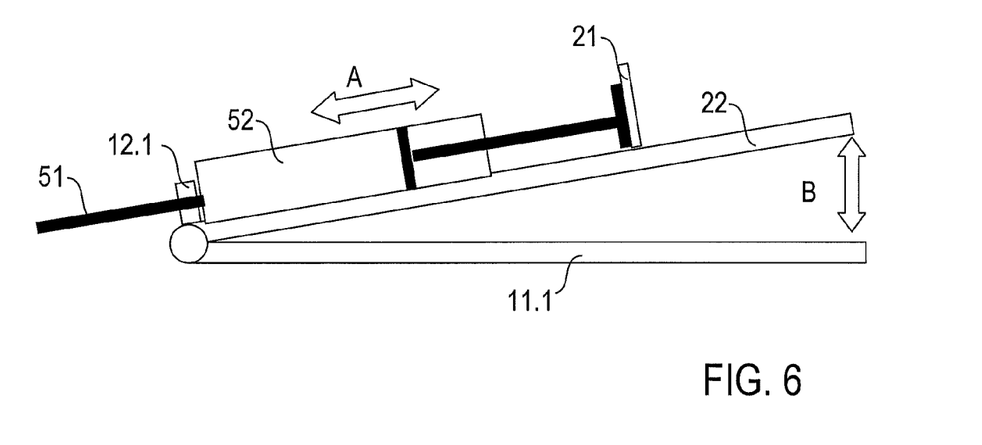

The guide tube 12 or the stop ring 12.1 is connected firmly to the swivelling lever 22 and can be swivelled with the latter in a slot in the carrier part 11.

Figure 7:
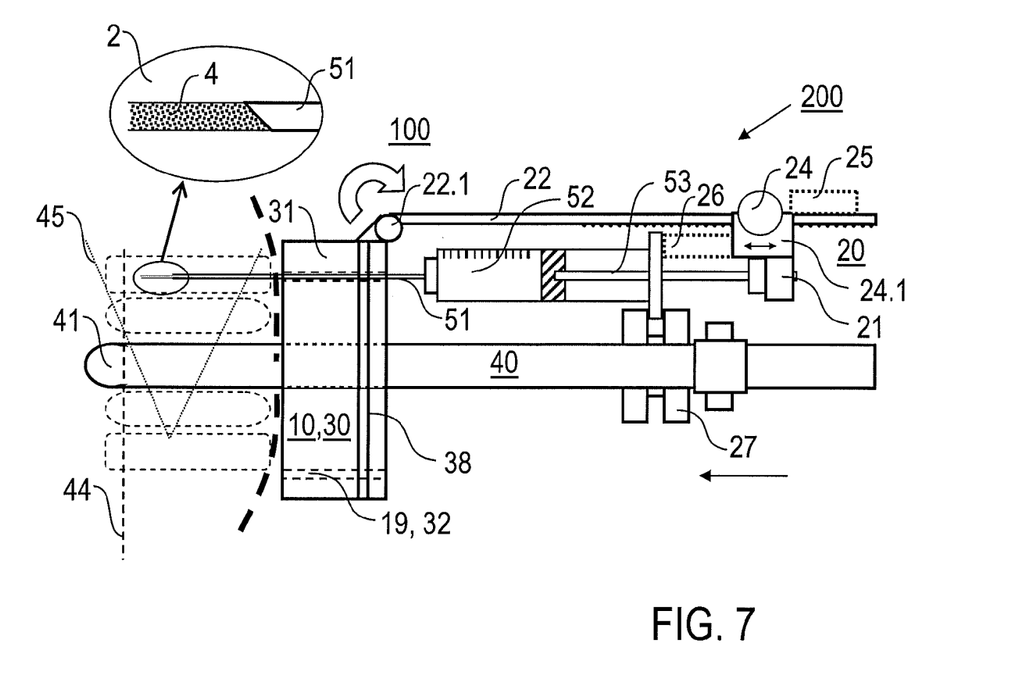
FIG. 7: a schematic side view of another embodiment of the injection device according to the invention.
Figure 8:
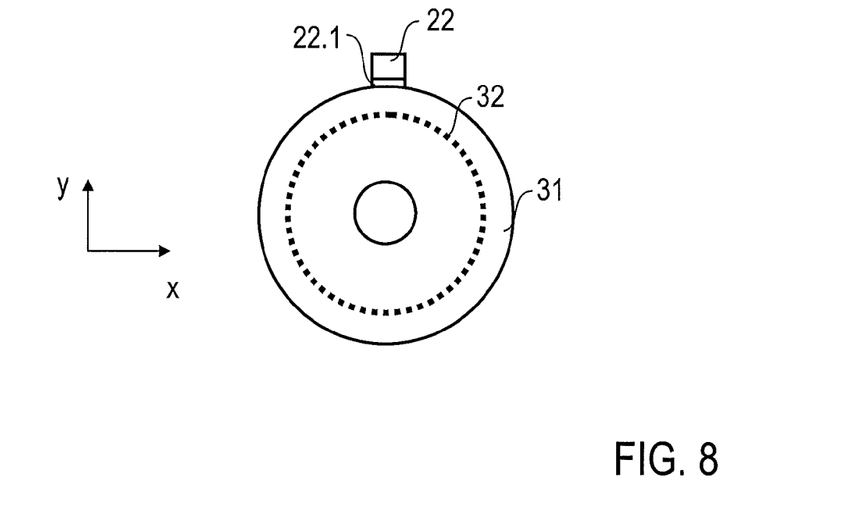
FIG. 8: a schematic front view of the embodiment of the injection device according to the invention shown in FIG. 7.

FIGS. 7 and 8 are schematic illustrations of features of further embodiments of the injection device according to the invention 100, in which it is provided in particular that the functions of the guide device 10 and of the holding device 30 are fulfilled together by the holding plate 31. The holding plate 31 forms an injection disk, which in these embodiments contains a plurality of azimuthally distributed through-holes 32 (see front view in FIG. 8), each of which forms a guide channel 19 for receiving the injection needle 51. Departing from FIG. 7, the through-holes can be arranged radially distributed. The holding plate 31 also forms a holder for the ultrasonic probe 40, the ultrasonic head 41 of which has a transverse acoustic plane 44 and a longitudinal acoustic plane 45.

FIG. 7 shows the injection syringe during the withdrawal movement. The enlargement in FIG. 7 shows the formation of an injection depot 4 with a linear injection volume in the external sphincter 2 in the injection channel of the withdrawn injection needle 51. The injection depot 4 contains e.g. myoblasts, in particular autologous myoblasts, which were obtained from the organism 1. The injection depot 4 has for example a diameter in the range from 200 µm to 1 mm and a length in the range from 5 mm to 10 cm.

The actuating device 20 comprises the swivelling lever 22, which is arranged with a joint 22.1 swivelling on the holding plate 31. The joint 22.1 can be moved in a ring guide 38 on an outer side of the holding plate 31, in order to align the swivelling lever 22 relative to one of the through-holes 32. The swivelling lever 22 carries a translation element 24 with a slide 24.1 that is displaceable on the swivelling lever 22. The actuating element 21 is fastened to the slide 24.1.

The swivelling lever 22 can be swivelled to a release position (not shown), in which the injection syringe 50 can be inserted in the holding plate 31. For injection, the swivelling lever 22 is swivelled to a stop position, in which the actuating element 21 is up against the syringe piston 53. In this state, the withdrawal movement of the injection syringe 50 and the injection into the tissue takes place. During injection, the injection syringe 50 is withdrawn alone or together with the ultrasonic probe 40 from the stationary holding plate 31.

According to a variant of the invention, the joint 22.1 can be omitted. In this case the swivelling lever 22 is mounted displaceably in the ring guide 38, but cannot be swivelled in the radial direction. The setting of the release position and of the stop position then takes place by translation of the slide 24.1.

According to the invention, it can be provided that the amount of injectable substance introduced into the tissue is set independently of the speed of the withdrawal movement. For this, an axial displacement of the actuating element 21 relative to the guide device 10 is provided during the withdrawal movement of the injection needle 51. The axial displacement of the actuating element 21 takes place e.g. with a motorized drive 25 or a transmission mechanism 26.

With the motorized drive 25, the actuating element 21 can be displaced opposite to the withdrawal movement. In this case the injection can be intensified, as the amount of substance that is injected in unit length is greater than with a stationary actuating element 21. With the transmission mechanism 26, the actuating element 21 can be displaced in the same direction as the withdrawal movement, but at a speed that is lower than the speed of the withdrawal movement of the injection needle 51 and of the syringe body 52. In this case the amount of substance injected in unit length is reduced. With the components 25 and 26 it is therefore possible to provide a gear transmission, by which the quantity of cells injected per mm of withdrawal path can be increased or reduced as required.

The transmission mechanism 26 forms a connection between the syringe body 52 and the actuating element 21, in particular with the slide 24.1 of the translation element 24. The transmission mechanism 26 contains a gearing mechanism, for instance a lever mechanism or a sliding gear transmission, with which the length of the transmission mechanism 26 can be varied in the axial direction. During the withdrawal movement of the injection syringe 50, the syringe body 52 also displaces, via the transmission mechanism 26, the slide 24.1 with the actuating element 21. The gearing mechanism is set up such that the speed of the actuating element 21 is less than the speed of the syringe body 52. A variant of the transmission mechanism 26 is shown in FIG. 9.

Typically, the withdrawal movement of the syringe body 52 is effected manually. Alternatively, according to another embodiment of the invention, a motorized drive 27 can be provided for movement of the syringe body 52 and the syringe needle 51, as shown schematically in FIG. 7.

Figure 9:
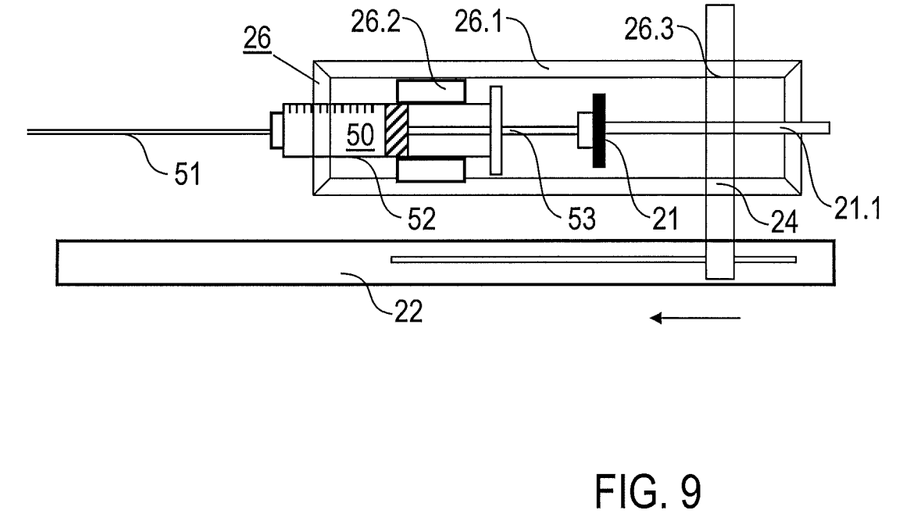
FIG. 9: a schematic sectional view of an embodiment of a transmission mechanism used according to the invention.

FIG. 9 shows a schematic sectional view of an embodiment of a transmission mechanism 26 used according to the invention, which has a sleeve part 26.1 and a connecting piece 26.2. The sleeve part 26.1 is connected via a screw thread 26.3 to the translation element 24, which is arranged displaceably on the swivelling lever 22 (see also FIGS. 1, 4, 7). The syringe body 52 is fixed with the connecting piece 26.2 in the sleeve part 26.1. The actuating element 21 is connected via a threaded bar 21.1, which projects through the translation element 24 and is locked against twisting, to the sleeve part 26.1. The screw thread 26.3 has a larger thread pitch than the threaded bar 21.1. By turning the sleeve part 26.1, the syringe body 52 with the syringe needle 51 can be withdrawn, while at the same time the threaded bar 21.1 and the actuating element 21 are withdrawn at a lower speed.

Figure 10:
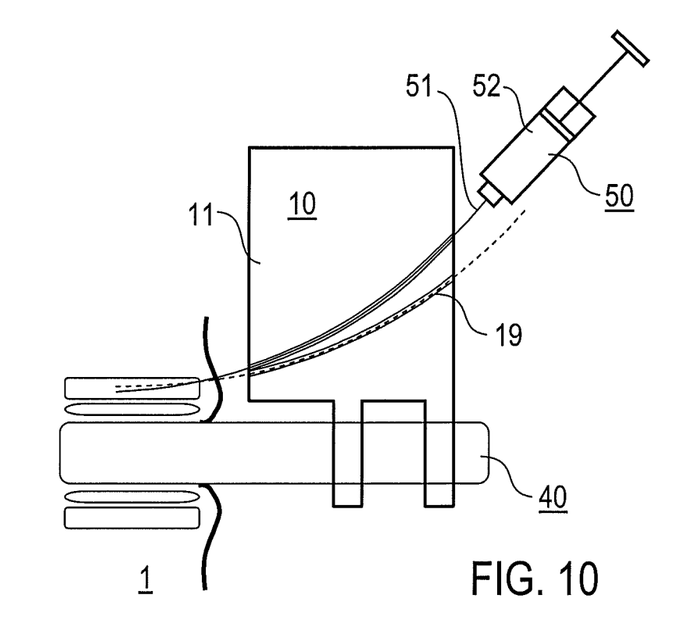
FIG. 10: a schematic illustration of a guide device for a curved injection needle.

Another embodiment of the guide device 10 used according to the invention is shown schematically in FIG. 10 (without the actuating device), in which one or more curved guide channels 19 are provided in the carrier part 11. In this embodiment the injection angle is set by advancing the injection needle 51 of the injection syringe 50 through one of the guide channels 19 with the desired orientation relative to the tissue.

According to a modified variant of the embodiment of the invention shown in FIG. 10, at least one straight guide channel can be provided in the carrier part 11. With the straight guide channel, a fixed injection angle is also specified. The guide channel performs the function of guiding the injection needle 51 and forming a stop for the syringe body 52.

The preferred application of the invention in the treatment of faecal incontinence is described in the following. The injection device according to the invention is preferably used for the treatment of faecal incontinence with live muscle cells. By injecting cultured muscle cells in the sphincter muscle of the colon, the contractile force is increased and therefore continence is restored. When the treatment is carried out especially preferably with autologous cells, the following steps are provided: (a) muscle biopsy, (b) isolation of cells, (c) cultivation of muscle cells, in particular myoblasts (d) formation of the injectable substance and (e) injection into the sphincter muscle.

In steps (a) to (c), preferably myoblasts are cultured. Biopsy and culture techniques that are known per se are employed. Which muscle is used for the biopsy is not critical. From the sample (0.5-2 g), muscle stem cells are isolated and multiplied (several hundred million). The cells are either packaged directly in syringes or are applied as a cellular pellet to the treatment site. A suspension of skeletal muscle cells in a culture medium is prepared in step (d). The culture medium comprises e.g. a physiological solution (e.g. with common salt, phosphate buffer), a cell culture medium with autologous serum. The suspension contains e.g. 10 million cells per milliliter. Then the syringe body of the injection syringe is filled.

Alternatively it is possible for the suspension of skeletal muscle cells to be formed by means of a double syringe with two syringe chambers. The cells are arranged in one syringe chamber, whereas a medium that is suitable for forming a gel together with the cells is arranged in the other syringe chamber. Said medium comprises e.g. autologous plasma. The fibrin contained in plasma can form a gel with calcium. On simultaneous injection from both syringe chambers, there is thorough mixing of the medium with the cells. Advantageously, the cells are thus embedded in the injection channel as a gel pad. This would prevent the risk of wash-out. The myoblasts would dissolve the fibrin gel again, so that there would not be any disturbing effects on fibre formation.

The charged injection syringe is set in the injection device, and the injection needle is introduced, with ultrasonic monitoring, e.g. into the external sphincter muscle, without injuring other layers of the rectum. Puncture preferably takes place at a distance from the anus of at least 1 cm, to reduce any risk posed by germs. During the treatment, altogether e.g. 100 million cells are applied in several depots or strips. On this basis cell therapy is carried out on the external sphincter.

Alternatively or additionally, smooth muscle cells or precursor cells that differentiate into smooth muscle cells can be injected into the internal sphincter.

The features of the invention disclosed in the above description, the drawings and the claims may be of importance individually or in combination for the implementation of the invention in its various embodiments.

The invention claimed is:

1. An injection device, which is provided for injection into an organism, having an injection syringe with a syringe body accommodating an injection fluid, an injection needle and a piston device, comprising:

a guide device, which is adapted for receiving the injection syringe, wherein the injection needle and the syringe body are movable with an advance movement towards or a withdrawal movement from the organism relative to the guide device, an imaging probe, which is connected to the guide device, said imaging probe having an axial reference direction, and an actuating device having an actuating element, to which the injection syringe can be coupled and which is adapted for actuation of the injection syringe for injecting an injectable substance into the organism, wherein the guide device has a carrier part and a guide tube for receiving the injection needle, the guide tube being arranged so that it can swivel on the carrier part for setting an injection angle of the injection syringe relative to the axial reference direction, the injection angle is selected such that the injection needle is directed radially inwards and towards the axial centre of the imaging probe, the actuating element is arranged so that the piston device is released from the actuating device during the advance movement of the syringe body and the injection needle, and the actuating element forms a limit stop for the piston device of the injection syringe on the guide device, so that during the withdrawal movement, for an expulsion of injection fluid through the injection needle, the piston device performs an opposite movement relative to the injection needle and the syringe body.

2. The injection device according to claim 1, in which the actuating device has a positioning device, with which the actuating element is arranged on the guide device.

3. The injection device according to claim 2, in which the positioning device has a swiveling lever for aligning the actuating element relative to the guide device.

4. The injection device according to claim 2, in which the positioning device has a translation element for displacement of the actuating element relative to the guide device.

5. The injection device according to claim 4, in which the translation element has a transmission mechanism, with which the speed of the displacement of the actuating element relative to the speed of the withdrawal movement of the injection needle can be adjusted.

6. The injection device according to claim 4, in which the translation element comprises a motorized drive, with which the actuating element can be displaced relative to the guide device.

7. The injection device according to claim 1, in which the actuating element is arranged on the positioning device such that it can be swiveled.

8. The injection device according to claim 1, in which the guide tube is arranged with a pivot bearing and a translational bearing on the carrier part.

9. The injection device according to claim 1, in which the orientation of the injection syringe can be adjusted with a swiveling lever of the actuating device, with the guide tube or a stop ring being secured on the swiveling lever for guiding the injection needle.

10. The injection device according to claim 1, which comprises:
a holding device with a holding plate, which can be placed on the organism and extends along a radial reference plane, wherein
the guide device is connected to the holding plate and the holding plate has at least one through-hole through which the injection needle can pass.

11. The injection device according to claim 10, in which the holding device has a holding frame, in which the holding plate is arranged rotatably.

12. The injection device according to claim 10, in which the holding plate has a plurality of through-holes, each of which forms a guide channel of the guide device for receiving the injection needle.

13. The injection device according to claim 1, wherein the imaging probe, is connected to the holding device.

14. The injection device according to claim 13, in which the holding device has an axially extending holding arm, which is connected to the holding plate and on which the imaging probe-is arranged displaceably.

15. Medical equipment, which is adapted for injection of an injectable substance into an organism, comprising:
an injection device according to claim 1, and
wherein the injection syringe is arranged in the guide device of the injection device.

16. The medical equipment according to claim 15, in which an imaging probe is arranged displaceably on a holding arm of a holding device of the injection device, and
the guide device is arranged displaceably on the imaging probe.

17. A method of injection of an injectable substance into an organism, using east one of the injection device according to claim 1 and an injection equipment that includes the injection device, the method including the step:
injection of the injectable substance during a withdrawal movement of the injection syringe from the organism.

18. The method according to claim 17, with the steps:
positioning of the holding device on the organism, so that the guide device has a predetermined position relative to an injection site in the organism,
inserting of the injection syringe in the guide device and advancing the injection syringe until the injection needle reaches the injection site,
aligning of the actuating element on the guide device, and
withdrawing of the injection syringe with simultaneous injection of the substance into the organism.

19. The method according to claim 18, with the further step:
positioning of an imaging probe on the holding device or outside of the injection equipment and imaging of the injection site.

20. The method of claim 18, wherein the injected substance is formed linearly.

21. An injection device, which is provided for injection into an organism, having an injection syringe with a syringe body accommodating an injection fluid, an injection needle and a piston device, comprising:
a guide device, which is adapted for receiving the injection syringe, wherein the injection needle and the syringe body are movable with an advance movement towards or a withdrawal movement from the organism relative to the guide device,
an imaging probe, which is connected to the guide device, said imaging probe having an axial reference direction, and
an actuating device having an actuating element, to which the injection syringe can be coupled and which is adapted for actuation of the injection syringe for injecting an injectable substance into the organism, wherein
the guide device has a carrier part and a guide tube for receiving the injection needle, the guide tube being arranged so that it can swivel on the carrier part for setting an injection angle of the injection syringe relative to the axial reference direction,
the injection angle is selected such that the injection needle is directed radially inwards and towards the axial centre of the imaging probe,
the actuating element is arranged so that the actuating element does not engage the piston device, and the piston device is released from the actuating element of the actuating device, during the advance movement of the syringe body and the injection needle, and
the actuating element engages the piston device and forms a limit stop that prevents rearward movement of the piston device of the injection syringe on the guide device during the withdrawal movement of the injection needle and the syringe body, so as to cause an expulsion of injection fluid through the injection needle, and so that the injection needle and the syringe body perform an opposite movement relative to the piston device during the withdrawal movement.

* * * * *